(12) United States Patent
Mottola et al.

(10) Patent No.: US 6,537,266 B1
(45) Date of Patent: Mar. 25, 2003

(54) PUNCTURE GUARD FOR CATHETER WIRE

(75) Inventors: Jim Mottola, South Jordan, UT (US); Stephanie S. Poulsen, Murray, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 09/532,204

(22) Filed: Mar. 22, 2000

(51) Int. Cl.[7] .............................................. A61M 39/20
(52) U.S. Cl. ...................... 604/523; 604/192; 604/263
(58) Field of Search ................. 604/192, 263, 604/264, 523

(56) References Cited

U.S. PATENT DOCUMENTS

| | | | |
|---|---|---|---|
| 3,324,853 A | * | 6/1967 | Czorny et al. .......... 604/263 X |
| 3,585,996 A | | 6/1971 | Reynolds et al. |
| 3,977,400 A | | 8/1976 | Moorehead |
| 4,096,860 A | | 6/1978 | McLaughlin |
| 4,215,703 A | | 8/1980 | Willson |
| 4,230,123 A | | 10/1980 | Hawkins, Jr. |
| 4,500,312 A | * | 2/1985 | McFarlane ................. 604/263 |
| 4,538,622 A | | 9/1985 | Samson et al. |
| 4,650,472 A | | 3/1987 | Bates |
| 4,652,256 A | | 3/1987 | Vaillancourt |
| 4,875,481 A | | 10/1989 | Higgins |
| 4,968,307 A | | 11/1990 | Dake et al. |
| 5,009,391 A | | 4/1991 | Steigerwald |
| 5,051,109 A | * | 9/1991 | Simon .................... 604/263 X |
| 5,062,836 A | | 11/1991 | Wendell |
| 5,117,839 A | | 6/1992 | Dance |
| 5,195,980 A | | 3/1993 | Catlin |
| 5,250,034 A | | 10/1993 | Appling et al. |
| 5,250,036 A | * | 10/1993 | Farivar ....................... 604/164 |
| 5,267,979 A | | 12/1993 | Appling et al. |
| 5,334,160 A | | 8/1994 | Ellis |
| 5,354,275 A | | 10/1994 | Behnke et al. |
| 5,358,495 A | | 10/1994 | Lynn |
| 5,376,077 A | | 12/1994 | Gomringer |
| 5,405,323 A | | 4/1995 | Rogers et al. |
| 5,421,349 A | | 6/1995 | Rodriguez et al. |
| 5,484,419 A | | 1/1996 | Fleck |
| 5,665,073 A | | 9/1997 | Bulow et al. |
| 5,676,671 A | | 10/1997 | Inoue |
| 5,836,965 A | | 11/1998 | Jendersee et al. |
| 5,858,002 A | | 1/1999 | Jesch |
| 5,951,517 A | | 9/1999 | Lampropoulos et al. |

FOREIGN PATENT DOCUMENTS

EP 0476 796 b1 12/1997

OTHER PUBLICATIONS

AngioDynamics®, *Infusion Systems*, Advertisement, Nov. 1998, pp. 1–6.

* cited by examiner

*Primary Examiner*—Kevin Lee
(74) *Attorney, Agent, or Firm*—Workman, Nydegger & Seeley

(57) ABSTRACT

An improved catheterization system includes: (i) a catheter system which receives a wire therein; and (ii) a puncture guard that flexibly, resiliently covers a portion of a wire extending from a proximal end of the catheter. Two-part and one-part embodiments of the puncture guard are available. The puncture guard is selectively mounted on a wire and/or onto a catheter through which the wire extends.

14 Claims, 6 Drawing Sheets

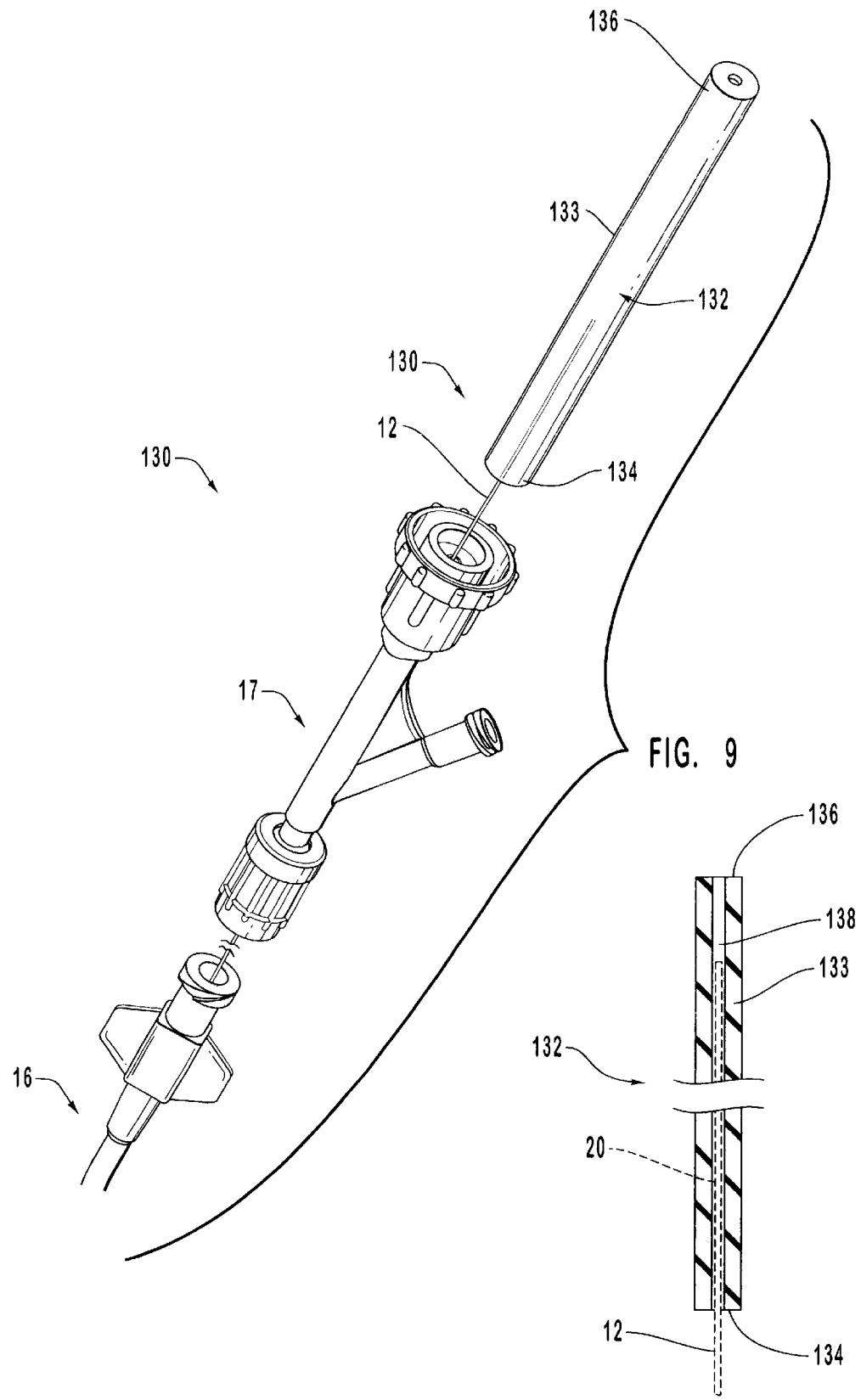

PUNCTURE GUARD FOR CATHETER WIRE

BACKGROUND OF THE INVENTION

1. The Field of the Invention

This invention is in the field of catheterization systems. More specifically, this invention is in the field of catheterization systems having one or more wires that extends through a catheter.

2. State of the Art

A variety of different wires are employed in conjunction with catheters inserted into the body of a patient. A guide wire, for example, may be initially inserted into a patient's blood vessel, after which a cannula is inserted over the guide wire into the blood vessel. The guide wire thus "guides" the cannula into a desired location within the blood vessel.

On some occasions, guide wires are extended through catheters, after which the catheter is either removed or is allowed to remain on the guide wire. For example, a catheter may be removed from the guide wire, after which a new catheter is inserted along the guide wire, thereby replacing the old catheter with a new catheter.

Occluding wires are employed within infusion catheters to cause fluid within the catheters to flow out of infusion holes in the catheters. Examples of such infusion catheters are disclosed in U.S. patent application Ser. No. 09/273,037, entitled Infusion System with Fixed Occluding Wire, to Mottola et al., filed Mar. 19, 1999, which is incorporated herein in its entirety by reference. A variety of other wires may be employed in catheter systems.

Catheters typically have a distal insertion end that is inserted into the body and a proximal, exposed end that is positioned outside of the body during use. In certain catheterization procedures, an end of an occluding wire, guide wire or other wire is allowed to extend out of the exposed proximal end of a catheter over an extended period of time.

As the wire extends out of the catheter, it is possible for the wire to puncture or scratch a practitioner's body, such as a hand, arm, or glove of a practitioner. A wire can also scratch a patient in whom a catheter is inserted. However, it is important that the wire be readily accessible to the practitioner for use during the catheterization procedure.

There is, therefore, a need in the art to protect a practitioner and a patient from an occluding wire, guide wire or other wire extending from a catheter, while nevertheless allowing the practitioner to readily access the wire when needed.

SUMMARY AND OBJECTS OF THE INVENTION

It is, therefore, an object of the invention to provide a catheterization system having a puncture guard for a catheter wire.

It is another object of the invention to provide a catheterization system having a puncture guard that provides convenient access to a catheter wire when desired.

It is another object of the invention to provide a catheterization system having a puncture guard that can move when the practitioner desires to adjust the position of a catheter wire.

It is another object of the invention to provide a resilient, flexible puncture guard.

The present invention relates to a puncture guard and an improved catheterization system employing the puncture guard. The improved catheterization system comprises: (i) a catheter system which receives a wire therein; and (ii) a puncture guard that flexibly, resiliently covers a portion of a wire extending from a proximal end of the catheter system. The catheter system may comprise an infusion catheter or a variety of other catheters that employ a wire.

The phrase "catheter system" as employed in this specification and the appended claims relates to: (i) a catheter; or (ii) a catheter and one or more adaptors configured to be coupled to the catheter. The puncture guard of the present invention may be coupled directly to a catheter but is preferably coupled indirectly to the catheter by being coupled to an adaptor, which is coupled to the catheter. Examples of adaptors, catheters, and wires that may be employed in the present invention are disclosed in U.S. patent application Ser. No. 09/273,037 entitled "Infusion System with Fixed Occluding Wire," filed Mar. 19, 1999, to Mottola, et al, which is incorporated herein in its entirety be reference.

A variety of different embodiments of the puncture guard of the present invention may be employed. One embodiment of a puncture guard comprises a flexible, resilient tube that is selectively mounted on a portion of a wire extending from the proximal end of the catheter. The tube covers the proximal end of the wire, preventing the wire from puncturing or scratching a practitioner or patient, yet still allowing a flexible wire to move if the practitioner desires to move the wire out of a certain area, for example. Thus, in one embodiment, the puncture guard couples to the wire, but is not mounted on the catheter system.

Another embodiment of a puncture guard comprises a flexible, resilient tube that covers a portion of the wire extending from the proximal end of the catheter system and selectively couples to the catheter system. A distal end of the tube is configured to be selectively coupled to the proximal end of a catheter system.

Yet another embodiment of a puncture guard of the present invention comprises: (i) a hollow rigid member; and (ii) a hollow resilient, flexible member selectively coupled thereto. The preferred embodiment of the hollow rigid member comprises a hollow rigid body and a gripping flange extending distally from the rigid body. The gripping flange is configured to be selectively coupled to the proximal end of the catheter system.

The puncture guard can be conveniently manufactured in conjunction with an adaptor and/or a catheter to which the puncture guard is selectively coupled. One example of a system configured to receive a wire therein during a catheterization procedure comprises a puncture guard and an adaptor. The puncture guard can be manufactured to be selectively coupled to the adaptor. The puncture guard and adaptor combination can serve collectively as a system that can be employed in conjunction with a variety of different catheters.

One advantage of the puncture guard of the present invention is the flexible nature of at least a portion of the puncture guard. Since the puncture guard is at least partially flexible, it is possible to move a flexible wire and the puncture guard, e.g., by temporarily bending the puncture guard flexible portion and the wire to a desired location. This allows the practitioner to move the wire when needed for a particular procedure. Nevertheless, the practitioner is protected from the proximal end of the wire.

Another advantage of the puncture guard of the present invention is the fact that the flexible member is preferably configured in the form of a sleeve. Since the sleeve has openings at both ends, a wire can be removed from or inserted into the catheter through the sleeve.

Yet another advantage of the preferred puncture guard of the present invention is the removable nature of the puncture guard. Since the preferred puncture guard is removable, it is possible to remove the puncture guard, place a wire into the catheter, then mount the puncture guard over the wire, for example. Optionally, the wire is extended through the puncture guard.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 9 is a perspective, exploded view of another catheterization system of the present invention having an alternate puncture guard from that of FIGS. 1 and 5.

FIG. 10 is a cross-sectional view of the puncture guard of FIG. 9, the puncture guard covering a portion of a wire shown in phantom lines.

DETAILED DESCRIPTION OF THE INVENTION

Figure 1:
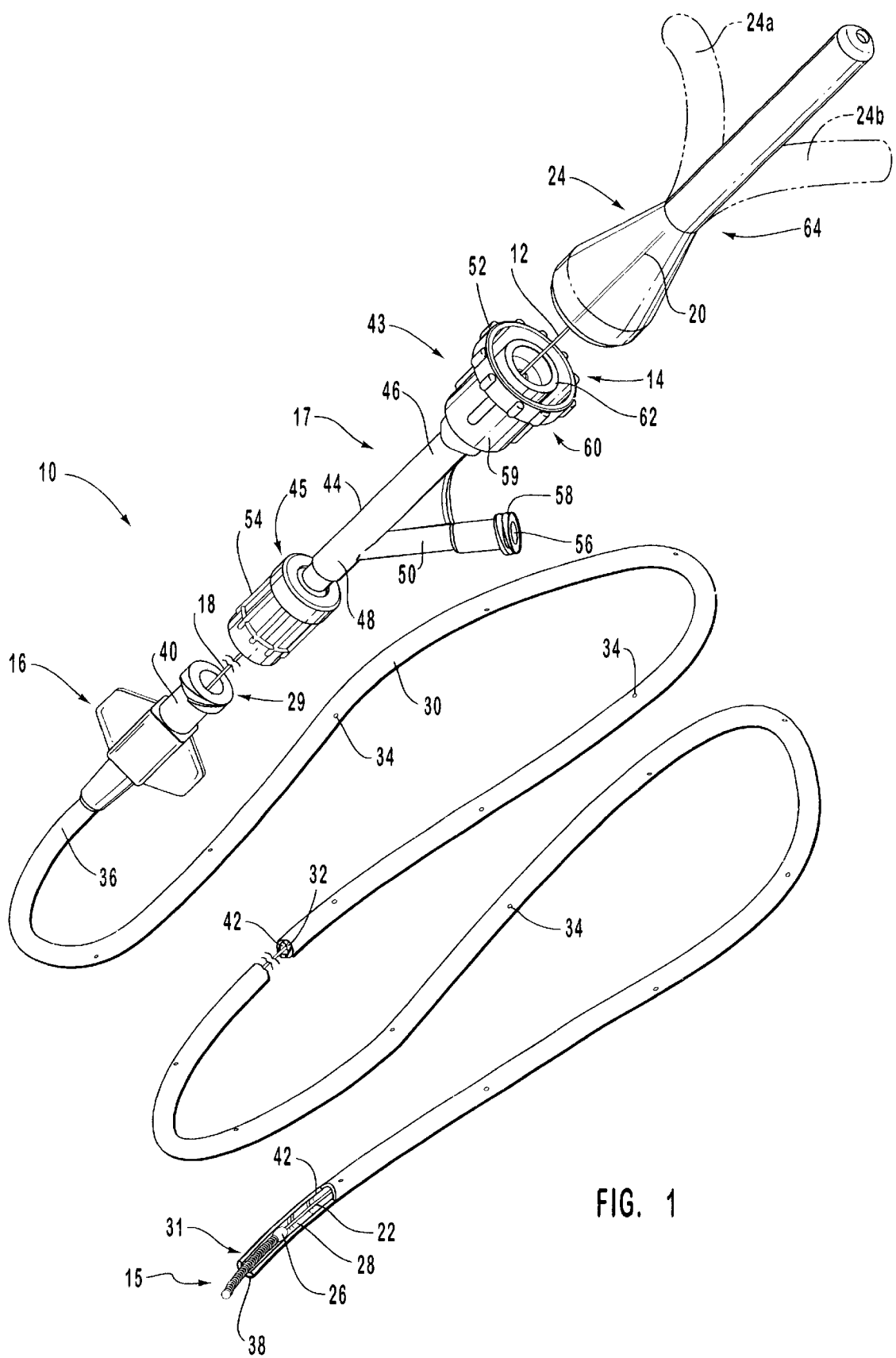
FIG. 1 is a perspective, exploded view of a catheterization system of the present invention, the system having a puncture guard.

An example of a catheterization system 10 of the present invention is shown in FIG. 1. Catheterization system 10 is configured for percutaneous catheterization of a blood vessel. Catheterization system 10 comprises: (i) an occluding wire 12; (ii) a catheter 16; (iii) an adaptor 17; and (iv) a puncture guard 24.

Occluding wire 12 comprises (i) an elongate wire body 18 having a proximal end 20 and a distal end 22 and (ii) an occluding tip 26 coupled to distal end 22 of elongate body 18. Occluding tip 26 may be integrally coupled to wire body 18 or may be coupled thereto through adhesion, welding, or another bonding method.

Catheter 16 has a proximal end 29 and a distal end 31. Catheter 16 comprises a hollow cannula 30 shown in a partial cross sectional, cut away view in FIG. 1 having (i) a cannula wall 32; (ii) a proximal end 36 defining a proximal opening; (iii) a distal end 38 defining a distal opening; and (iv) a lumen 28 extending from proximal end 36 to distal end 38. Lumen 28 is sized to receive occluding tip 26 of wire 12. Wall 32 has a plurality of infusion holes 34 extending therethrough. Catheter 16 thus comprises an infusion catheter although a variety of other catheters may be employed with the puncture guard of the present invention.

Catheter 16 further comprises a hollow hub 40 coupled in fluid communication with proximal end 36 of cannula 30. Hub 40 is configured to receive occluding tip 26 of occluding wire 12 therethrough. Hub 40 of catheter 16 may include a male or female lure lock connector or another connector, for example. One catheter presently preferred is a single lumen catheter, although a variety of different catheter embodiments may be employed in the present invention.

As mentioned and as shown in FIG. 1, catheterization system 10 further comprises puncture guard 24. Puncture guard 24 is configured to be selectively coupled to catheter 16. Coupling of a puncture guard of the present invention to a catheter of the present invention may be direct, i.e. by coupling the puncture guard directly to the hub of the catheter.

However, in the embodiment of FIG. 1, puncture guard 24 is configured to be selectively coupled to catheter 16 by being selectively coupled to adaptor 17 which is selectively coupled to hub 40 of catheter 16. Adaptor 17 has a proximal end 43 and a distal end 45. Adaptor 17 comprises a hollow, tubular body 44 having a proximal end 46, a distal end 48, and a fluid supply port such as hollow secondary access tube 50 coupled in fluid communication with tubular body 44 between proximal end 46 and distal end 48.

A hub 52 of adaptor 17 is coupled to proximal end 46 of tubular body 44. A rotatable connector 54 is coupled to distal end 48 of tubular body 44. Connector 54 selectively couples hub 40 of catheter 16 to tubular body 44 of adaptor 17 and hub 52 is configured to be selectively coupled to puncture guard 24.

Connector 54 may comprise a male or female lure lock component, for example, for coupling tubular body 44 to hub 40 of catheter 16 such that adaptor 17 is in fluid communication with catheter 16. Secondary access tube 50 has a central bore 56 therethrough so as to be in fluid communication with tubular body 44. A male or female lure lock connector 58 or other connector is disposed on tube 50 in order to couple tube 50 in fluid communication with a fluid source. Secondary access tube 50 can be used to introduce fluids or medical devices into catheter 16.

Adaptor 17 is an example of means for coupling catheter 16 in fluid communication with a fluid source. A fluid source coupled to connector 58 of tube 50, for example, may allow fluid to flow through bore of tube 50. The fluid then flows into catheter 16 and out of infusion holes 34.

In one preferred embodiment, adaptor 17 comprises a hemostasis valve assembly 60 and hub 52 comprises a rotating knob 59 of hemostasis valve assembly 60. The hemostasis assembly 60 may comprise a slit valve or a touhi-borst valve, for example. One primary purpose of the valve assembly 60 is to maintain a fluid seal around elongate wire body 18 or another instrument to prevent the leaking of blood and other bodily fluids as elongate wire body 18 or another instrument is positioned within valve assembly 60.

Hub 52 preferably comprises a cylindrically shaped hollow proximal end portion 62 configured to receive occluding tip 26 therethrough and configured to receive puncture guard 24 thereon. End portion 62 may serve as a proximal end wall of a rotating knob 59 of valve assembly 60, for example. The cylindrically shaped hollow proximal end portion 62 is merely one example, however, of a structure configured for selectively mating with puncture guard 24.

Puncture guard 24 is press fit onto hub 52 of adaptor 17. Puncture guard 24 selectively mounts onto end portion 62 in a mating relationship. However, the puncture guard of the present invention may selectively couple to the proximal hub of the adaptor or directly to the hub of the catheter in a variety of different manners, such as through the use of lure lock components, mating threads, or a variety of different couplings. In yet another embodiment of a puncture guard (discussed below with respect to FIGS. 9 and 10), the puncture guard selectively mounts onto the proximal end of the wire without coupling to the catheter.

Figure 2:
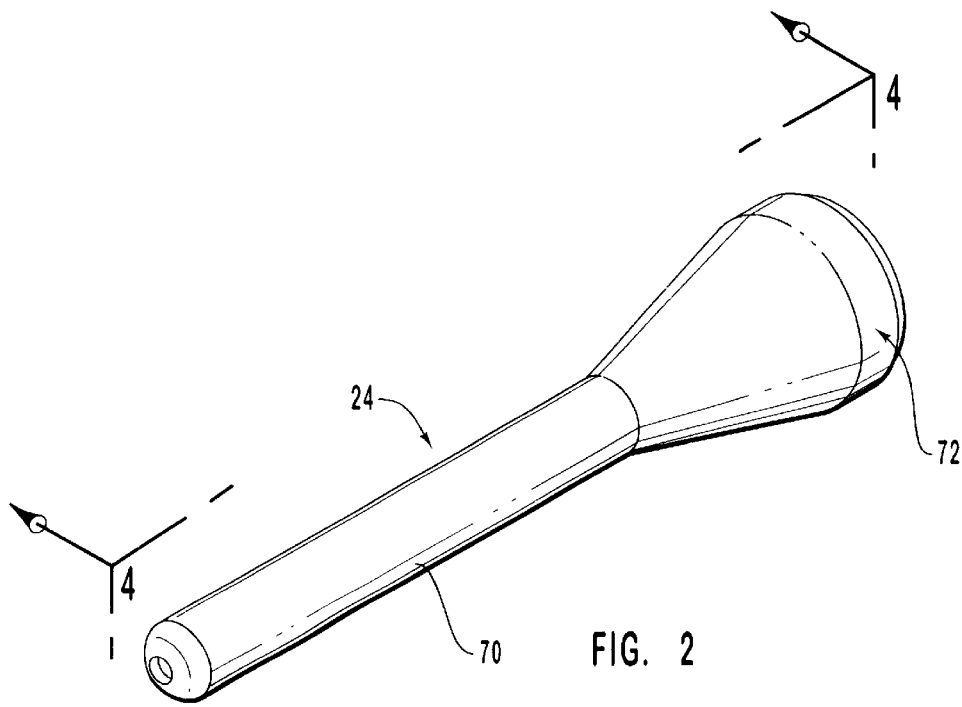
FIG. 2 is a perspective view of the puncture guard of FIG. 1.
Figure 3:
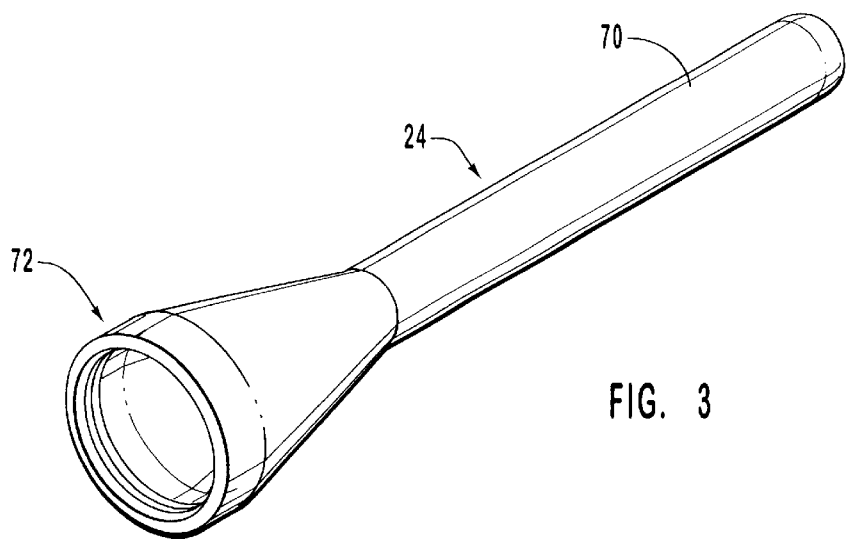
FIG. 3 is another perspective view of the puncture guard of FIG. 1.
Figure 4:
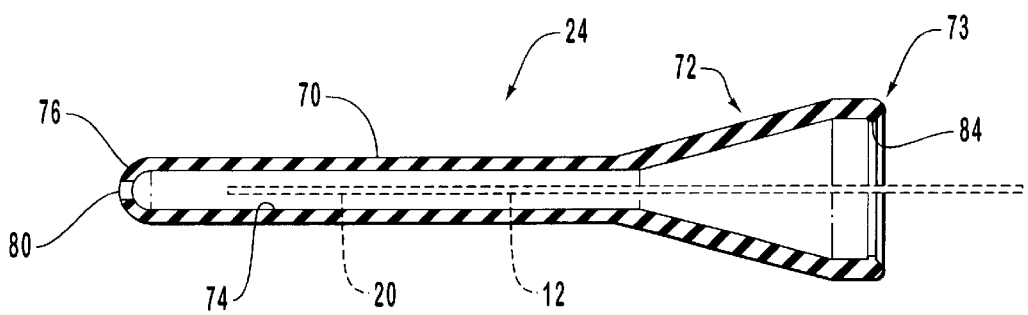
FIG. 4 is a cross sectional view of the puncture guard of FIG. 1 with a wire disposed therein, the puncture guard covering a portion of the wire.

With reference now to FIGS. 2, 3, and 4, puncture guard 24 of FIG. 1 comprises (i) a hollow proximal puncture guard body 70; and (ii) a substantially circular distal gripping flange 72 extending distally from hub body 70. Flange 72 has a wider diameter than body 70. Flange 72 is configured to be selectively mounted on hollow cylindrical end portion 62 of adaptor 17.

Puncture guard 24 is a hollow, tubular sleeve member having (i) body 70; and (ii) flange 72 integrally coupled to body 70. Puncture guard 24 thus has a distal end 73, a proximal end 76 and an interior surface 74 extending from proximal end 76 to distal end 73.

Body 70, as shown in FIGS. 2–4, is an elongate hollow member having a substantially uniform cross section in a central portion thereof and is rounded at proximal end 76. Also at proximal end 76, body 70 narrows to a small opening 80 configured to receive a wire therethrough. This may be advantageous if wire 12 needs to be threaded into or out of opening 80 for a particular procedure, for example.

Gripping flange 72 is a hollow conically shaped member having an annular ridge 84 therein which forms a fluid tight seal on cylindrical end portion 62 of hub 52 of adaptor 17. Optionally, snap tabs are mounted in a substantially circular configuration to thereby selectively grip cylindrical end portion 62.

As indicated, puncture guard 24 is a resilient, flexible sleeve that is selectively, removably coupled to the proximal end of a catheter system. The flexible nature of puncture guard 24 has a variety of different advantages. First, puncture guard 24 is flexible such that a practitioner moving against puncture guard 24 can move puncture guard 24 to a desired location and move a flexible wire that is disposed therein. Examples of directions of movement for puncture guard 24 are shown at 24a and 24b in phantom lines in FIG. 1. It may be desireable to tape the puncture guard 24 in an out-of-the-way location against a patient's body for example.

Since puncture guard 24 comprises a resilient material, puncture guard 24 retains its shape until bent in a desired direction. One advantage of the resilient nature of puncture guard 24 is that puncture guard 24 does not droop onto wire 12. Another advantage of the resilient nature of puncture guard 24 is that it can be readily mounted onto a catheter system. Guard 24 also retains its shape regardless of whether a wire is disposed therethrough at a particular time.

Body 70 of puncture guard 24 is thus an example of a covering means for flexibly, resiliently covering a portion of a wire extending from a means for defining a fluid flow pathway, such as catheter 16 and/or adaptor 17. Distal flange 72 is an example of coupling means for selectively coupling body 70 to a means for defining a fluid flow pathway.

Puncture guard 24 is made from an elastomeric material. For example, puncture guard 24 may be comprised of a variety of different materials, such as polyurethane, nylon, polyethylene, rubber, or silicone.

Proximal end 20 of wire 12 (shown in phantom lines) is shown as being covered by puncture guard 24 in FIG. 4. In use, by disposing puncture guard 24 over proximal end 20, such as shown in FIG. 4, wire 12 is prevented from puncturing or scratching a practitioner or patient.

Catheter 16 serves as an example of means for defining a fluid flow pathway. Similarly, adaptor 17 of FIG. 1 serves as an example of means for defining a fluid flow pathway. Finally, catheter 16 and adaptor 17 of FIG. 1 coupled to catheter 16 collectively serve as an example of means for defining a fluid flow pathway. The puncture guard of the present invention can be selectively coupled to any of these means for defining a fluid flow pathway during a catheterization procedure, for example.

Figure 5:
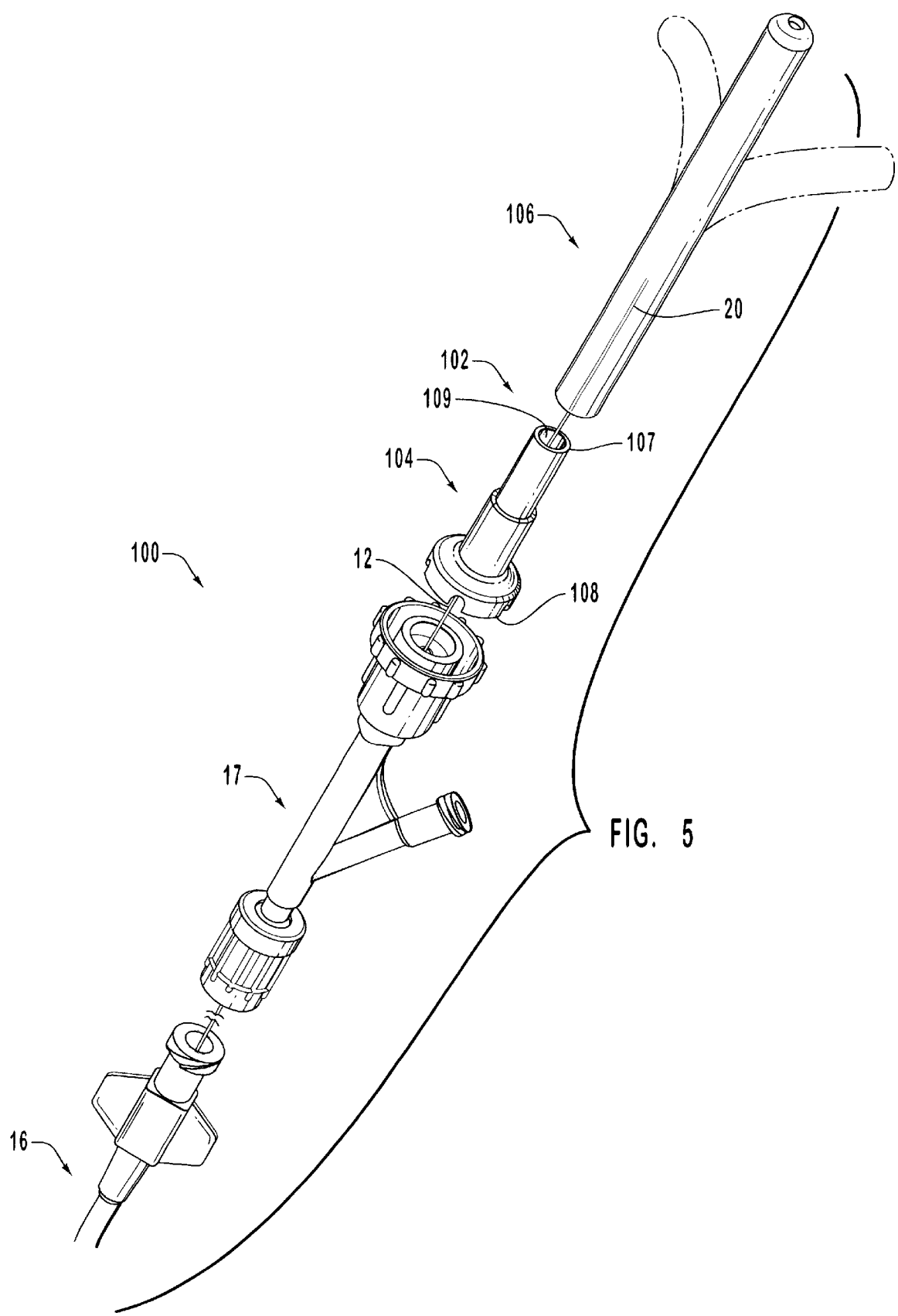
FIG. 5 is a perspective view of another catheterization system of the present invention having an alternate puncture guard from that of FIG. 1.

FIG. 5 demonstrates another example of a catheterization system 100 of the present invention. Catheterization system 100 comprises wire 12, catheter 16, adaptor 17, and two-part puncture guard 102. Two-part puncture guard 102 comprises a rigid distal member 104 and a flexible, resilient proximal member 106. Rigid member 104 comprises a rigid, hollow cap that is selectively, removably coupled to a proximal end of a catheter system. In the embodiment of FIG. 5, rigid member 104 is selectively, removably coupled to adaptor 17. In another embodiment, however, the rigid hollow cap of the present invention is selectively, removably coupled directly to the hub of a catheter.

Tubular cap 104 has a proximal end 107, a distal end 108 and an interior surface 109 extending therebetween. Proximal member 106 comprises a resilient, elastomeric sleeve that is selectively, removably coupled to proximal end 107 of cap 104.

As shown in FIG. 5, each of cap 104 and sleeve 106 are hollow, tubular members such that proximal end 20 of wire extends therethrough when cap 104 and sleeve 106 are mounted on adaptor 17. Also as shown in FIG. 5, since elastomeric sleeve 106 is flexible, sleeve 106 can flex between a variety of different positions as shown by the phantom lines of sleeve 106 depicted in FIG. 5. Puncture guard 102 is further depicted in FIGS. 6–8. Thus sleeve 106 and a flexible wire enclosed therein can be selectively moved for a particular procedure, if desired.

Figure 6:
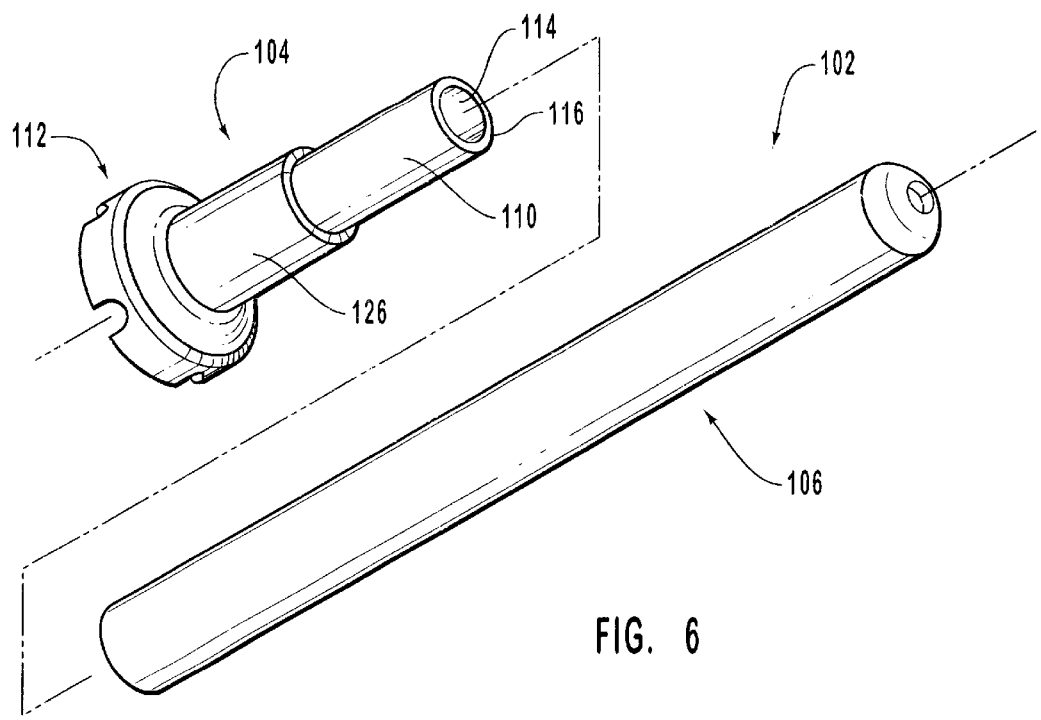
FIG. 6 is a perspective, exploded view of the puncture guard of FIG. 5.
Figure 7:
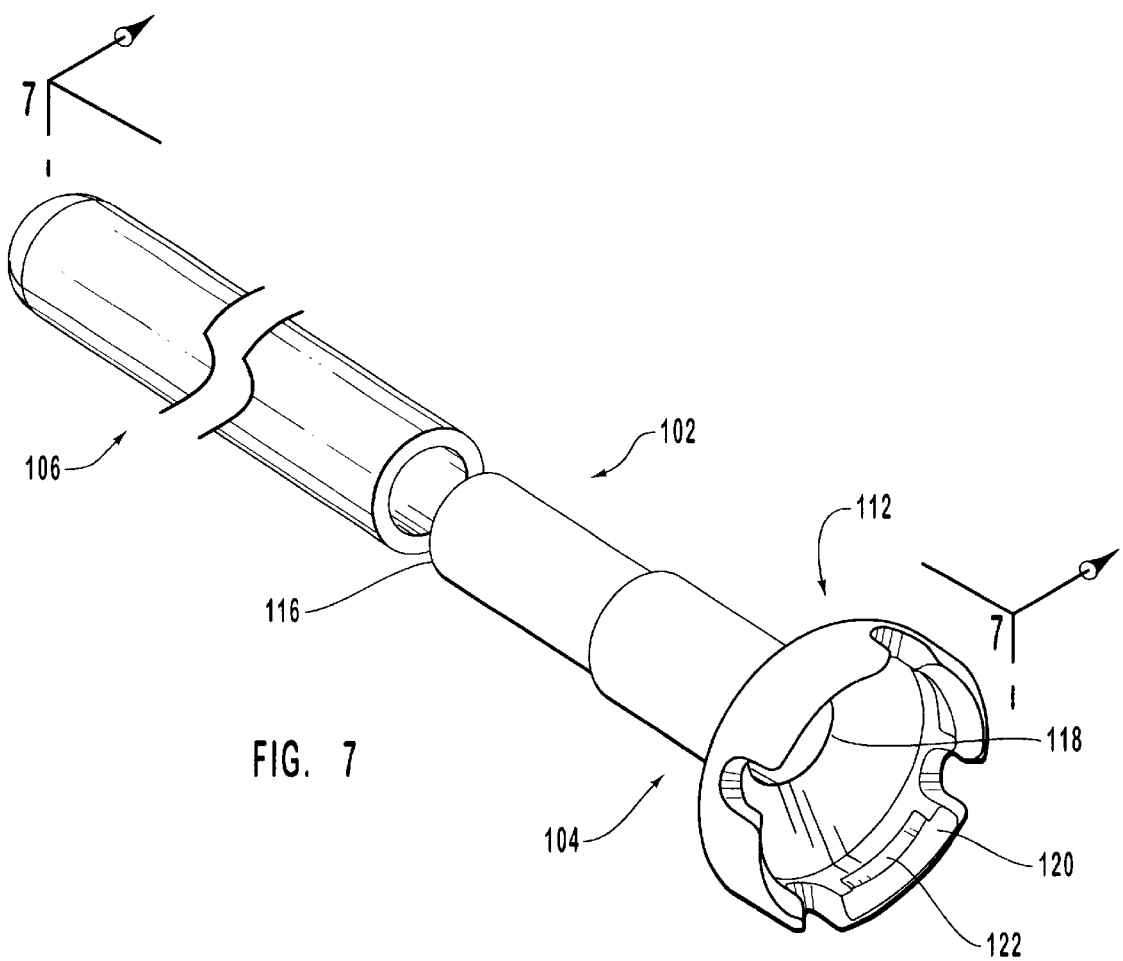
FIG. 7 is a perspective, exploded, cutaway view of the puncture guard of FIG. 5.
Figure 8:
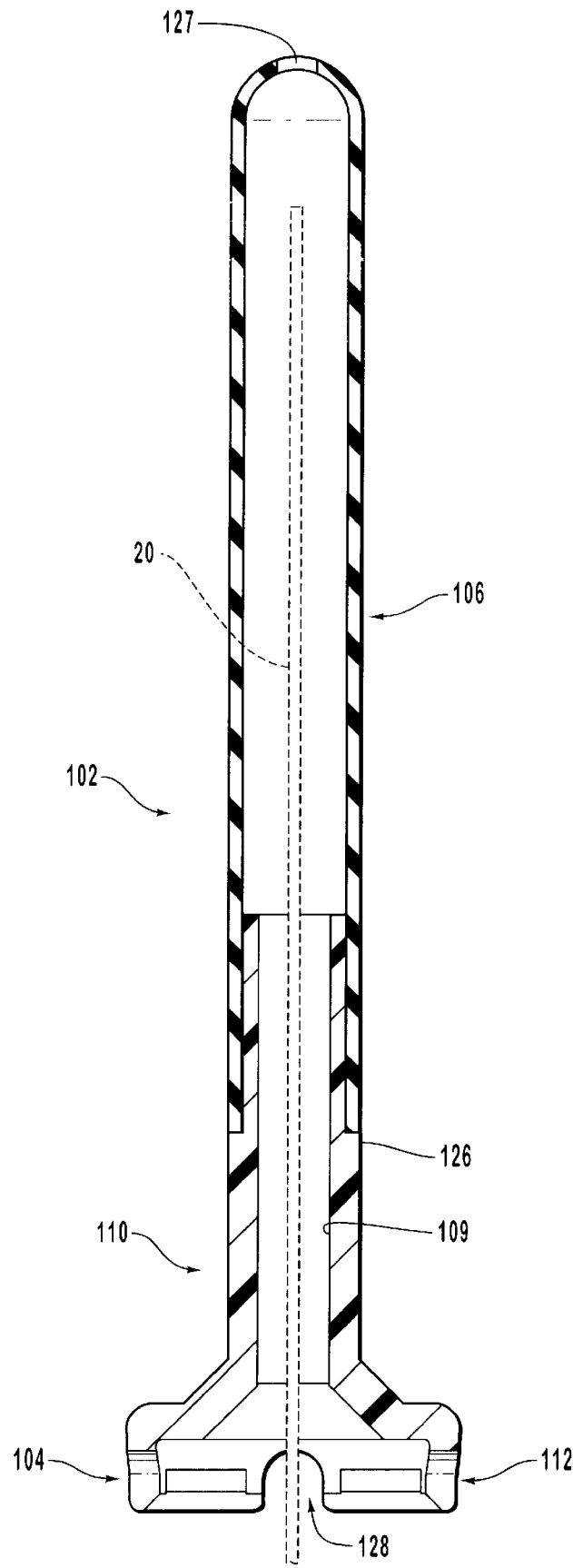
FIG. 8 is a cross sectional view of the puncture guard of FIG. 5 having a wire therein shown in phantom lines, the puncture guard covering a portion of the wire.

As shown in FIGS. 6–8, hollow cap 104 comprises a hollow cap body 110 and a substantially circular gripping flange 112 extending distally from body 110. Distal gripping flange 112 is configured to be selectively, removably mounted on hollow cylindrical end portion 62 of adaptor 17. A hollow interior surface 114 of cap body 110 extends from a proximal tip 116 of cap body 110 to a distal face 118 of cap body 110. Distal flange 112 extends from hollow body 110.

Gripping flange 112 comprises a plurality of snap tabs 120 extending distally from face 118 of body 110. Snap tabs 120 are oriented in a substantially circular configuration to thereby selectively grip a cylindrical end portion 62 of hub 52 of adaptor 17 therebetween. In one embodiment, snap tabs 120 move resiliently outwardly when the practitioner couples cap 104 to hub 52 of adaptor 17. To increase the gripping action of tabs 120 internal ridges 122 are positioned on respective snap tabs 120. Optionally, a circular ridge is disposed about cylindrical end portion 62 of hub 52 and ridges 122 selectively snap over the circular ridge.

Cap 112 acts as a seat on which to mount elastomeric sleeve 106. As further shown in FIGS. 5–7, body 110 of cap 112 has an annular ridge 126 on an exterior portion thereof. Ridge 126 allows elastomeric sleeve 106 to be mounted on body 110 adjacent ridge 126, such that a sufficient amount of sleeve 106 is mounted on body 110 to retain sleeve 106 on cap 112 until a user desires to remove sleeve 106.

One advantage of two-part puncture guard 102 is that rigid cap 104 can be selectively mounted onto a hub of an adaptor or a catheter and readily form a convenient, reliable snap-fit. The snap-fitting capability of rigid cap 104 enables a practitioner to snap a rigid cap onto a hub, which can provide a reliable interference fit. Sleeve 106 is readily mounted on cap 104 either before or after cap 104 is mounted onto the hub.

A proximal end 20 of a wire may be protected by puncture guard 102 by being mounted within puncture guard 102, as shown in FIG. 8. Puncture guard 102 has a proximal opening 127 (opening 127 in sleeve 106) and a distal opening 128 (opening 128 in cap 104) and a passageway extending therebetween. One advantage of having an open proximal end and an open distal end in the puncture guard of the present invention is that the practitioner can have access to both the proximal and distal ends of the puncture guard. This access can allow the practitioner to feed a wire through the proximal end and into the catheter and/or adaptor. The open proximal end also allows the practitioner to completely or partially remove a wire through puncture guard 102.

Sleeve 106 serves as an example of covering means for flexibly, resiliently covering a portion of a wire extending from a means for defining a fluid flow pathway. Cap 104 serves as an example of coupling means for selectively coupling the covering means to a means for defining a fluid flow pathway.

Rigid cap 104 may be comprised of a polycarbonate material, ABS plastic or a variety of other materials, for example, while resilient, elastomeric member 106 may also be comprised of a variety of different materials, such as polyurethane, nylon, polyethylene, rubber, and silicone, for example.

FIGS. 9 and 10 demonstrate another example of a catheterization system 130 of the present invention comprising a puncture guard 132 selectively mounted on a wire, such as occluding wire 12 or another wire, extending proximally from a catheter 16. Puncture guard 132 comprises a flexible, resilient member in the form of a sleeve. Sleeve 132 has an elongate body 133 having a distal end 134 having a distal opening, a proximal end 134 having a proximal opening, and a hollow interior surface 138 between ends 134, 136. Sleeve 132 is configured to be selectively mounted directly on a wire extending proximally from the proximal end of the means for defining a fluid flow pathway.

Sleeve 132 is another example of covering means for flexibly, resiliently covering a portion of a wire extending from a catheter. Configuring sleeve 132 such that sleeve 132 can be mounted on wire 12, such as shown in FIGS. 9 and 10, is an example of coupling means for selectively coupling sleeve to wire 12.

As shown in FIGS. 9 and 10, for example, in use, sleeve 132 slides onto the proximal end 20 of a wire 12, thereby preventing the wire from puncturing or scratching a practitioner or a patient. Sleeve 132 can selectively abut the proximal end of adaptor 17, for example. Resilient, elastomeric sleeve member 132 may be comprised of a variety of different materials, such as polyurethane, nylon, polyethylene, rubber, and silicone, for example.

Thus, as shown in FIGS. 1–4, in one embodiment a puncture guard 24 of the present invention in the form of a resilient, elastomeric sleeve is selectively coupled to a catheter system. As shown in FIGS. 5–8, in another embodiment, a puncture guard 102 comprising a rigid member and a resilient, elastomeric sleeve is selectively coupled to a catheter system. However, as shown in FIGS. 9 and 10, in another embodiment, a puncture guard 132 comprises a resilient, elastomeric sleeve selectively mounted on a proximal portion of a wire without requiring the sleeve to be coupled to the catheter.

However, it will be appreciated that a variety of different resilient, flexible members may be employed in the present embodiment to cover a proximal end of a wire, such as a cap comprising a hollow, resilient, flexible member having an opening at only one end, rather than at two open ends as employed in sleeves. Such a resilient, flexible hollow cap may have an elongate body or be in the form of a ball, square, semicircular, hemispherical, or other shape and may be selectively, removably coupled to a catheter system, wire, or to the proximal end of a rigid cap such as cap 104, for example. Such hollow caps with an opening at only one end are additional examples of covering means for flexibly, resiliently covering a portion of a wire extending from a means for defining a fluid flow pathway.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. In a catheterization system adapted for percutaneous catheterization of a patient's blood vessel, and wherein the system includes an adaptor through which one end of an occluding wire is inserted into the blood vessel and the other end remains outside of the patient, a puncture guard for protecting the medical practitioner from being accidentally punctured by the end of the wire that remains outside of the patient, and which does not interfere with the bending characteristics of the wire, the puncture guard comprising:

a first portion which comprises an elongated, hollow covering means for completely enclosing therewithin the end of the wire that remains outside of the patient in order to protect a medical practitioner from accidental puncture, said first portion further comprising a flexible, resilient material that is sufficiently bendable so as not to interfere with the bending characteristics of the wire; and a second portion which comprises a means for securing the first portion to the adaptor.

2. The puncture guard of claim 1, wherein the covering means comprises a sleeve configured to receive a portion of the wire therethrough.

3. The puncture guard of claim 1, wherein the means for securing comprises a rigid cap having a hollow interior surface extending from a proximal end to a distal end thereof.

4. The puncture guard of claim 3, wherein the covering means is selectively coupled to the rigid hollow cap.

5. The puncture guard of claim 1, wherein the second portion comprises a distal flange that has a wider diameter than the body of the sleeve.

6. The puncture guard of claim 1, wherein the first portion comprises a sleeve having a proximal end, a distal end, and an interior surface extending from the proximal end to the distal end.

7. The puncture guard of claim 6, wherein the second portion comprises a flange portion and a body portion, the sleeve being mounted on the body portions.

8. The puncture guard of claim 7, wherein the flange portion is selectively mounted on the end of a tubular body.

9. The puncture guard of claim 1, wherein the flexible, resilient material is comprised of an elastomeric material.

10. The puncture guard of claim 1, wherein the second comprises an annular ridge, and wherein the first portion is configured to be mounted on the second portion adjacent the annular ridge.

11. In a catheterization system adapted for percutaneous catheterization of a patient's blood vessel, and wherein the system includes an adaptor through which a one end of an occluding wire is inserted into the blood vessel and the other end remains outside of the patient, a puncture guard for protecting the medical practitioner from being accidentally punctured by the end of the wire that remains outside of the patient, and which does not interfere with the bending characteristics of the end of the wire, the puncture guard comprising:

a first portion which comprises an elongated, hollow cylindrically shaped member that has sufficient length to completely enclose therewithin the end of the wire that is outside of the patient, in order to protect a medical practitioner from accidental puncture, said first portion further comprising a flexible, resilient material that is sufficiently bendable so as not to interfere with the bending characteristics of the wire; and a second portion which comprises a flange, the first and second portions being joined to one another and the flange comprising means for coupling the puncture guard to the adaptor.

12. The puncture guard of claim 11, wherein the first portion and second portions are configured such that a wire selectively extends through the first and second portions when they are joined to one another.

13. The puncture guard of claim 11, wherein first portion is configured to be selectively mounted directly the end of the wire that remains outside the patient.

14. The puncture guard of claim 11, wherein the first portion is selectively and removably coupled to the second portion.

* * * * *

UNITED STATES PATENT AND TRADEMARK OFFICE
CERTIFICATE OF CORRECTION

PATENT NO.   : 6,537,266 B1                                                        Page 1 of 1
DATED        : March 25, 2003
INVENTOR(S)  : Jim Mottola and Stephanie S. Poulsen It is certified that error appears in the above-identified patent and that said Letters Patent is hereby corrected as shown below:

<u>Title page,</u>
Item [56], OTHER PUBLICATIONS, insert -- AngioDynamics®, <u>Uni*Fuse,</u>
Advertisement, on information and belief, available in the fall of 1998, p. 1. --

<u>Column 2,</u>
Line 18, change "be" to -- by --

<u>Column 9,</u>
Line 12, change "portions," to -- portion. --
Line 17, after "second" insert -- portion --

Signed and Sealed this

Second Day of September, 2003

JAMES E. ROGAN
*Director of the United States Patent and Trademark Office*